US012590332B2

(12) United States Patent (10) Patent No.: US 12,590,332 B2
Han et al. (45) Date of Patent: Mar. 31, 2026

(54) COMPOSITION FOR DIAGNOSING OR TREATING KIDNEY DISEASE

(71) Applicant: INJE UNIVERSITY INDUSTRY-ACADEMIC COOPERATION FOUNDATION, Gimhae-si (KR)

(72) Inventors: Sang-Youb Han, Goyang-si (KR); Dae-Young Hur, Busan (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 616 days.

(21) Appl. No.: 18/010,459

(22) PCT Filed: Jun. 15, 2021

(86) PCT No.: PCT/KR2021/007497
§ 371 (c)(1),
(2) Date: Dec. 15, 2022

(87) PCT Pub. No.: WO2021/256837
PCT Pub. Date: Dec. 23, 2021

(65) Prior Publication Data
US 2023/0304090 A1 Sep. 28, 2023

(30) Foreign Application Priority Data

Jun. 15, 2020 (KR) ........................ 10-2020-0072162
Jun. 15, 2021 (KR) ........................ 10-2021-0077253

(51) Int. Cl.
*C12Q 1/6883* (2018.01)
(52) U.S. Cl.
CPC ..... *C12Q 1/6883* (2013.01); *C12Q 2600/136* (2013.01); *C12Q 2600/158* (2013.01)
(58) Field of Classification Search
None
See application file for complete search history.

(56) References Cited

U.S. PATENT DOCUMENTS

2008/0096770 A1* 4/2008 McGinnis ............ C12Q 1/6876
506/10
2010/0222228 A1* 9/2010 Thielemans ......... C12Q 1/6883
435/7.1

FOREIGN PATENT DOCUMENTS

KR 10-2015-0031405 A 3/2015
KR 20150031405 A * 3/2015 ....... G01N 33/57449
KR 10-2051559 B1 12/2019
WO WO-2020033791 A1 * 2/2020 ......... C12N 15/1138

OTHER PUBLICATIONS

Li et al Nature Communications. 2017. 8:132, p. 1-14 (Year: 2017).*
Zeng et al J Cell Biochem. 120: 8676-8688 (Year: 2019).*
Gong et al Life. 10: 354, 7 pages (Year: 2020).*
International Search Report for PCT/KR2021/007497 mailed Sep. 13, 2021 from Korean Intellectual Property Office.
Han, Sy et al., "The Role of VSIG4 in the Mouse Model of Unilaterla Ureteral Obstruction", Kidney International Reports, Mar. 1, 2020, vol. 5, p. S76, abstract No. SAT-178.
Li, Y. et al. "Costimulatory molecule VSIG4 exclusively expressed on macrophages alleviates renal tubulointerstitial injury in VSIG4 KO mice", J Nephrol, 2014, vol. 27, pp. 29-36.
Li, Y. et al. "Expression of Vsig4 attenuates macrophage-mediated hepatic inflammation and fibrosis in high fat diet (HFD)-induced mice", Biochemical and Biophysical Research Cmmnunications, 2019, vol. 516, pp. 858-865.
Seung-Mi Kim et al. "Epstein-Barr virus-encoded latent membrane protein 1 induces epithelial to mesenchymal transition by inducing V-set Ig domain containing 4 (VSIG4) expression via NF-kB in renal tubular epithelial HK-2 cells", Biochemical and Biophysical Research Communications, 2017, vol. 492, pp. 316-322.
Xiao-dong Geng et al. "Identification of key genes and pathways in diabetic nephropathy by bioinformatics analysis", J Diabetes Investig, Jul. 2019, vol. 10, No. 4, pp. 972-984.

* cited by examiner

*Primary Examiner* — Carla J Myers
(74) *Attorney, Agent, or Firm* — Revolution IP, PLLC

(57) ABSTRACT
The present invention relates to a composition for diagnosing or treating kidney disease, and specifically, provides a composition for diagnosing kidney disease, including VSIG4 or a gene coding same as an active ingredient, and a pharmaceutical composition for preventing or treating kidney disease, including an expression or activity inhibitor for VSIG4 or a gene coding same as an active ingredient.

1 Claim, 6 Drawing Sheets

Specification includes a Sequence Listing.

[FIG. 1]
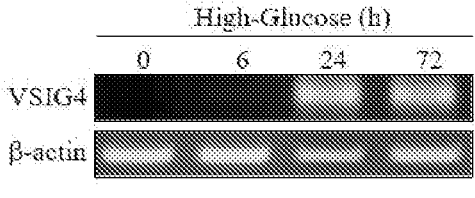
VSIG4 mRNA
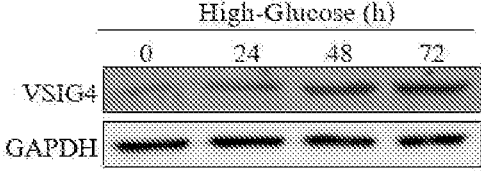
VSIG4 protein
[FIG. 2]
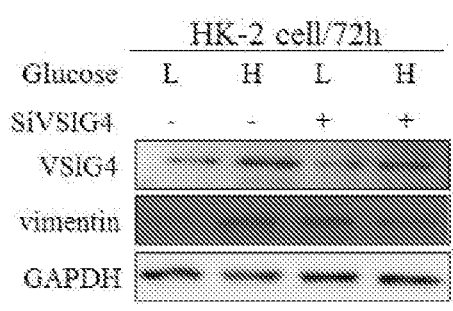
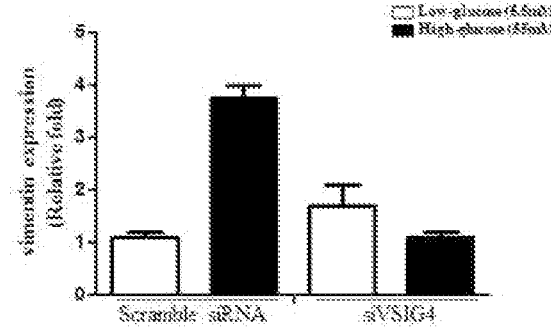

[FIG. 3]
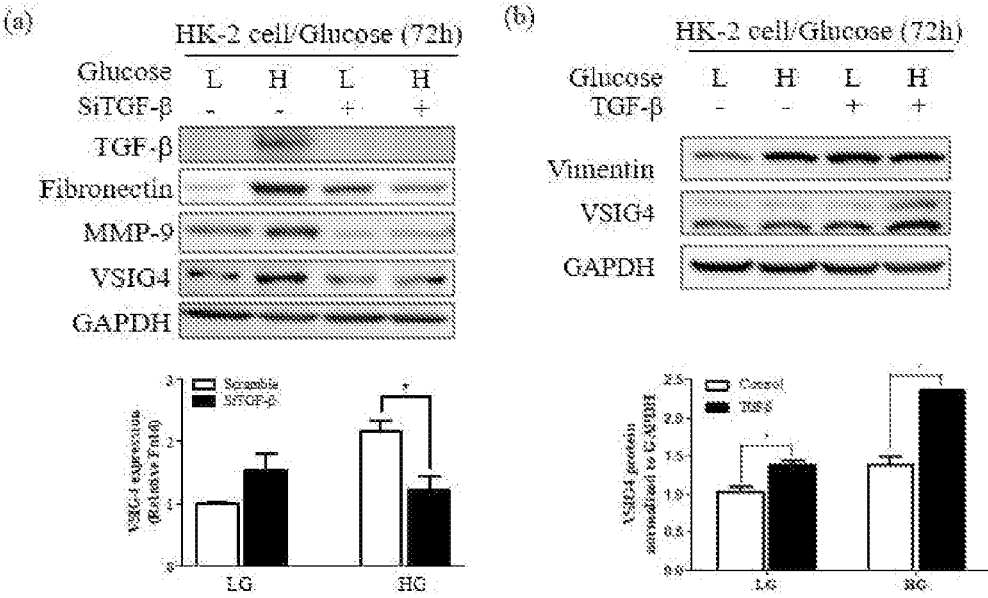
[FIG. 4]
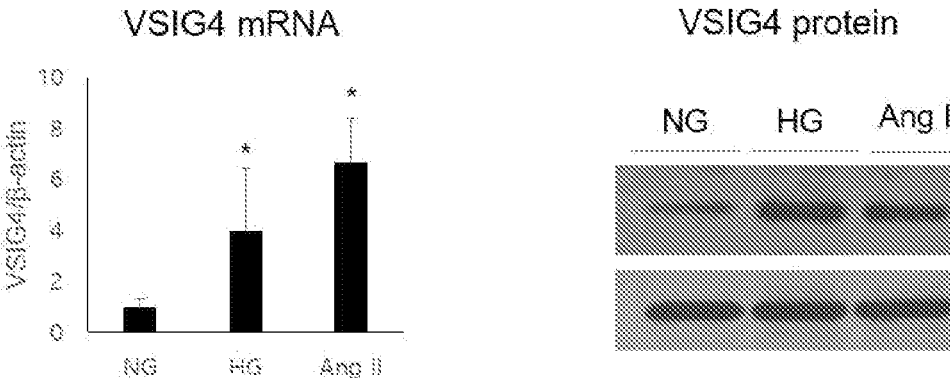

[FIG. 5]
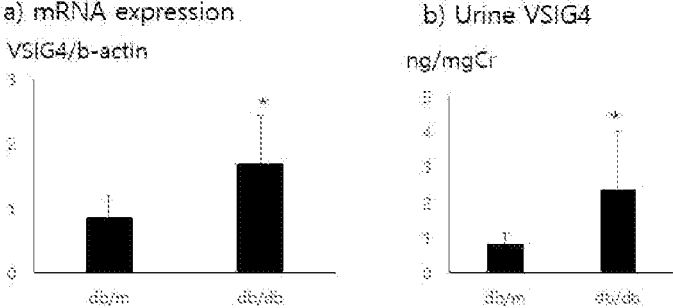
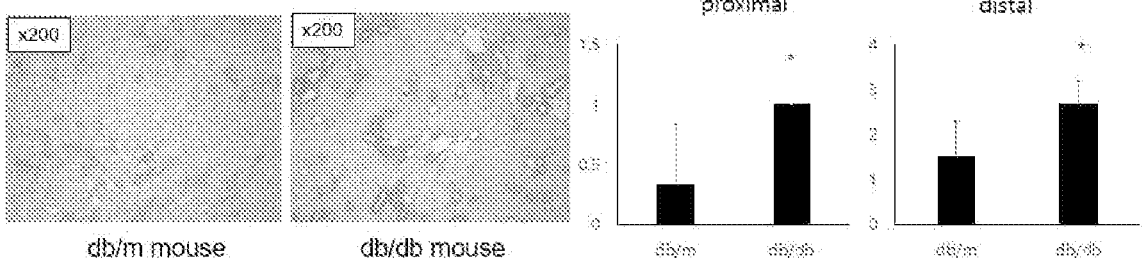
[FIG. 6]
albuminuria
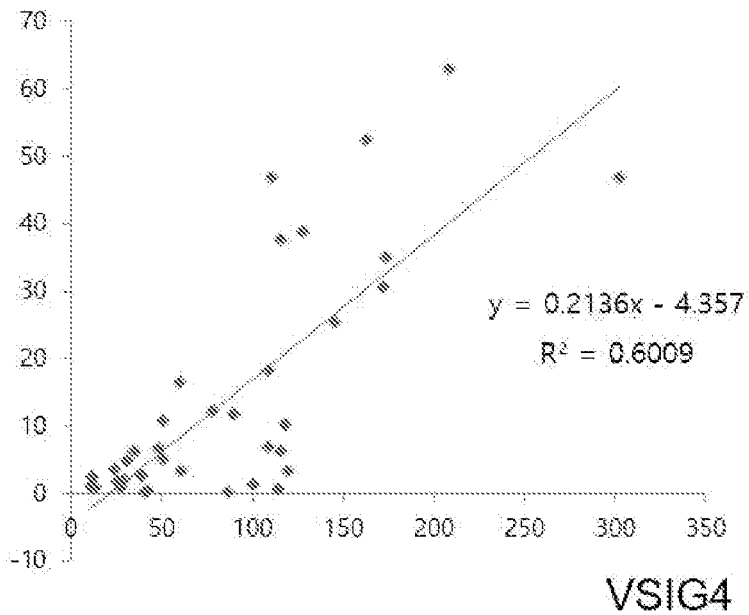

[FIG. 7]
a) Intrarenal VSIG4 mRNA
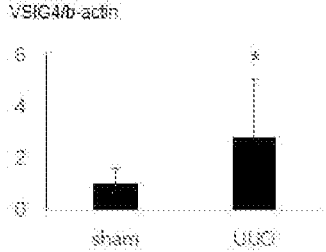
b) Urine VSIG4
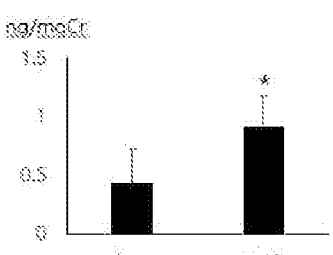
c) Immunohistochemistry
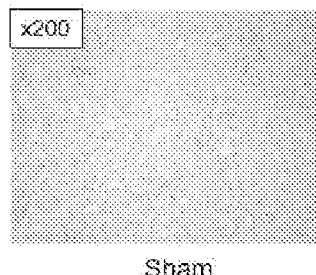
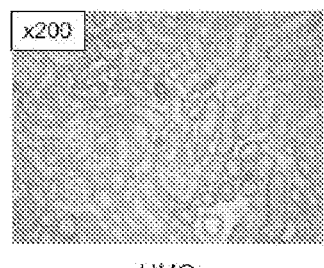
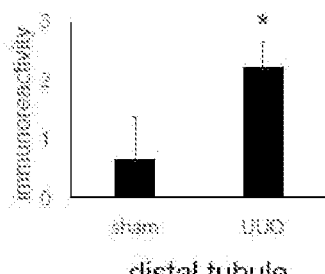
Sham                              UUO                              distal tubule
[FIG. 8]
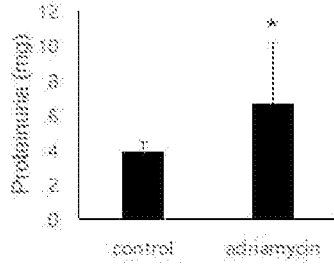
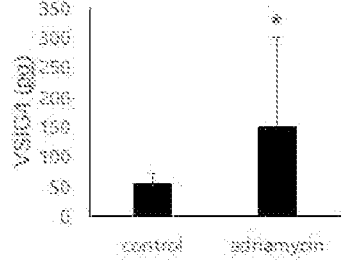
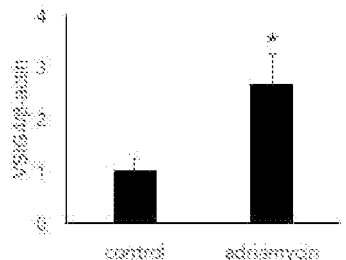

[FIG. 9]
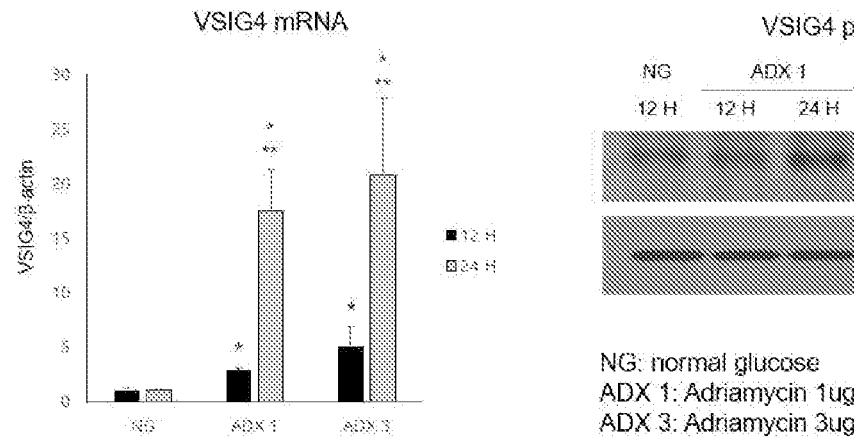
[FIG. 10]
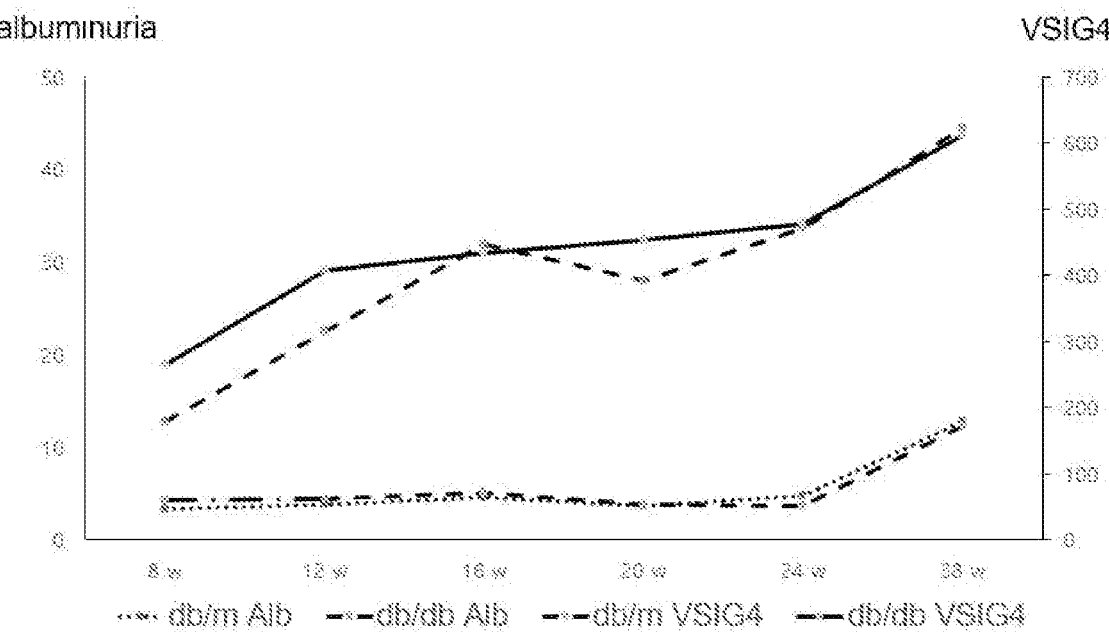

[FIG. 11]
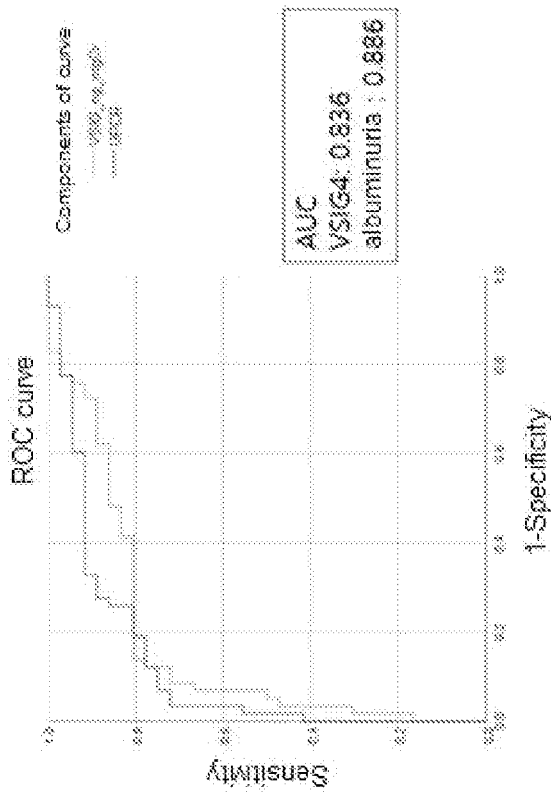
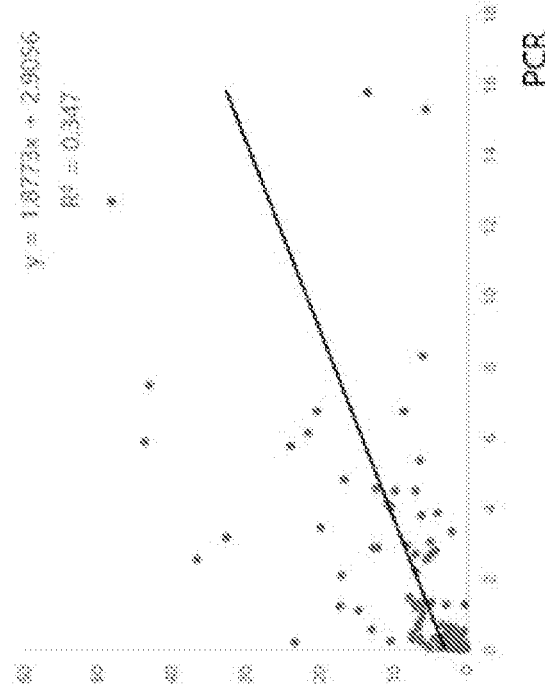

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: H VSIG4-f primer

<400> SEQUENCE: 1
aactcctgtc tccaagccc                                        19

<210> SEQ ID NO 2
<211> LENGTH: 20
<212> TYPE: DNA
<213> ORGANISM: Artificial Sequence
<220> FEATURE:
<223> OTHER INFORMATION: H VSIG4-r primer

<400> SEQUENCE: 2
gcagtgcaga aataggagcc                                       20

<210> SEQ ID NO 3
<211> LENGTH: 20
```

-continued

```
<212> TYPE: DNA
<213> ORGANISM: Artificial Sequence
<220> FEATURE:
<223> OTHER INFORMATION: beta-actin-f primer

<400> SEQUENCE: 3
gccgggacct gactgactac                                                   20

<210> SEQ ID NO 4
<211> LENGTH: 20
<212> TYPE: DNA
<213> ORGANISM: Artificial Sequence
<220> FEATURE:
<223> OTHER INFORMATION: beta-actin-r primer

<400> SEQUENCE: 4
tcttctccag ggaggagctg                                                   20

<210> SEQ ID NO 5
<211> LENGTH: 20
<212> TYPE: DNA
<213> ORGANISM: Artificial Sequence
<220> FEATURE:
<223> OTHER INFORMATION: M VSIG4-f primer

<400> SEQUENCE: 5
tccctggctt cctttcttct                                                   20

<210> SEQ ID NO 6
<211> LENGTH: 20
<212> TYPE: DNA
<213> ORGANISM: Artificial Sequence
<220> FEATURE:
<223> OTHER INFORMATION: M VSIG4-r primer

<400> SEQUENCE: 6
ccaaacccag gatttctcaa                                                   20

<210> SEQ ID NO 7
<211> LENGTH: 20
<212> TYPE: DNA
<213> ORGANISM: Artificial Sequence
<220> FEATURE:
<223> OTHER INFORMATION: beta-actin-f primer

<400> SEQUENCE: 7
ggactcctat gtgggtgacg                                                   20

<210> SEQ ID NO 8
<211> LENGTH: 20
<212> TYPE: DNA
<213> ORGANISM: Artificial Sequence
<220> FEATURE:
<223> OTHER INFORMATION: beta-actin-r primer

<400> SEQUENCE: 8
cttctccatg tcgtcccagt                                                   20
```

COMPOSITION FOR DIAGNOSING OR TREATING KIDNEY DISEASE

CROSS REFERENCE TO PRIOR APPLICATIONS

This application is a National Stage Application of PCT International Patent Application No. PCT/KR2021/007497 filed on Jun. 15, 2021, under 35 U.S.C. § 371, which claims priority to Korean Patent Application Nos. 10-2020-0072162 filed Jun. 15, 2020 and 10-2021-0077253 filed on Jun. 15, 2021, respectively, which are all hereby incorporated by reference in their entirety.

SEQUENCE LISTING

This application contains a Sequence Listing submitted via EFS-Web and hereby incorporated by reference in its entirety. The Sequence Listing is named SEQCRF_2280-427.txt, created on Dec. 13, 2022, and 1,941 bytes in size.

TECHNICAL FIELD

The present disclosure relates to a composition for diagnosing or treating kidney diseases and, more particularly, a composition for diagnosing kidney diseases including VSIG4 or a gene encoding the same as an active ingredient, and a composition for preventing or treating kidney diseases including an expression or activity inhibitor of VSIG4 or a gene encoding the same as an active ingredient.

BACKGROUND ART

Chronic kidney diseases is a very common, accounting for about 7-10% of the total population worldwide, while Korea also shows a similar pattern. In particular, the number of patients who are subjected to renal replacement therapy (hemodialysis, peritoneal dialysis, and kidney transplantation) due to end-stage renal failure reaches 1,600 per million people. The number is gradually increasing due to the recent increase in the elderly population, so does the number of patients receiving renal replacement therapy. Thereby, medical expenses for dialysis are also rising, having significant effects on medical expenses. Only 0.14% patients of the total population require dialysis, accounting for 3% of the total medical expenses.

The common finding of end-stage renal failure is kidney fibrosis. Kidney fibrosis begins to occur in glomerulus or renal tubules depending on the disease, but tubulointerstitial fibrosis is the final symptom. Various factors are known to be involved in kidney fibrosis.

Kidney fibrosis was accepted as an irreversible finding, but it was found that mesangial hypertrophy and tubulointerstitial fibrosis which are the major findings of kidney fibrosis were reduced 10 years after pancreatic transplantation in patients with type 1 diabetes-induced kidney damage. In other words, if hyperglycemia which is a main causal factor of diabetic nephropathy is overcome, kidney fibrosis may also be improved. Therefore, it indicates that the fibrosis of kidney is reversible, with a probability of restoring renal functions in patients with advanced kidney diseases when an appropriate treatment is applied.

For the treatment of chronic kidney diseases, currently relied on is conservative treatment such as smoking cessation and low-salt diet, low-protein diet, blood pressure control, hyperlipidemia management, and renin-angiotensin-aldosterone inhibitors. In spite of these efforts, when the renal function drops below 40%, further deterioration in the renal function is inevitable to eventually receive dialysis or transplantation. That is, at this stage, there is no other alternative without fundamentally treating the kidney fibrosis.

Despite various attempts to block each previously known stage of kidney fibrosis, there is still no drug that may completely block or reduce kidney fibrosis. Therefore, there is a need to discover a new target capable of inhibiting kidney fibrosis.

DISCLOSURE OF THE INVENTION

Technical Goals

An object of the present disclosure is to provide a biomarker composition including a novel target that is effective in diagnosing kidney diseases, and a composition and kit for diagnosing kidney diseases.

Another object of the present disclosure is to provide a method of providing information necessary for diagnosing kidney diseases using the target and a method of screening a therapeutic agent for kidney diseases.

Another object of the present disclosure is to provide a pharmaceutical composition and health functional food composition for preventing or treating kidney diseases.

Technical Solutions

In order to achieve the above object, the present disclosure provides a biomarker composition for diagnosing kidney diseases, including VSIG4 or a gene encoding the same as an active ingredient.

The present disclosure provides a composition for diagnosing kidney diseases, including an agent for measuring an expression level of VSIG4 as an active ingredient.

The present disclosure provides a kit for diagnosing kidney diseases, including the composition for diagnosis.

The present disclosure provides a method of providing information necessary for diagnosing kidney diseases, including measuring an expression level of VSIG4 or a gene encoding the same in a sample isolated from a subject suspected of having kidney diseases; and comparing the expression level of the VSIG4 or gene encoding the same with that of a normal control sample.

The present disclosure provides a method of screening a therapeutic agent for kidney diseases, including treating a biological sample isolated from a subject with a test substance; measuring an expression level of VSIG4 or a gene encoding the same in the sample treated with the test substance; and selecting a test substance in which the expression level of the VSIG4 or gene encoding the same is reduced compared to a control not treated with the test substance.

The present disclosure provides a pharmaceutical composition for preventing or treating kidney diseases, including an expression or activity inhibitor of VSIG4 or a gene encoding the same as an active ingredient.

In addition, the present disclosure provides a health functional food composition for preventing or ameliorating kidney diseases, including an expression or activity inhibitor of VSIG4 or a gene encoding the same as an active ingredient.

Advantageous Effects

A biomarker composition according to the present disclosure may effectively diagnose various kidney diseases, including kidney fibrosis, using VSIG4 or a gene encoding the same, which is found to be involved in progression of kidney damage or kidney fibrosis, such that it is possible to prevent or treat kidney diseases using an expression or activity inhibitor of the VSIG4 or gene encoding the same.

In addition, through rapid diagnosis and treatment for kidney fibrosis, it may help prevent or treat various diseases that cause kidney fibrosis.

BRIEF DESCRIPTION OF DRAWINGS

FIG. 1 shows changes in VSIG4 expression in renal tubular cells according to glucose treatment.

FIG. 2 shows changes in expression of VSIG4 and vimentin according to treatment of glucose and siVSIG4.

FIG. 3 shows changes in VSIG4 expression according to treatment of siTGF-β or TGF-β.

FIG. 4 shows change in VSIG4 expression of podocytes according to treatment of glucose and angiotensin II.

FIG. 5 shows changes in VSIG4 expression in a db/db type 2 diabetic mouse model.

FIG. 6 shows the relationship between albuminuria and VSIG4 expression in urine of a db/db type 2 diabetic mouse model.

FIG. 7 shows changes in VSIG4 expression in a unilateral ureteral obstruction (UUO) mouse model.

FIGS. 8 and 9 show changes in VSIG4 expression in an Adriamycin-induced renal injury model.

FIG. 10 shows changes in proteinuria and VSIG4 expression in a senescent mouse model.

FIG. 11 shows identification of VSIG4 expression patterns in a patient with type 2 diabetic nephropathy.

BEST MODE FOR CARRYING OUT THE INVENTION

Hereinafter, the present disclosure will be described in detail.

Since various mechanisms are involved in the pathogenesis of chronic kidney diseases, the present inventors assumed that it would be more effective to block the stage of kidney fibrosis, which is the final stage of kidney damage, rather than to block a single mechanism in the intermediate stage thereof, and thus completed the present disclosure by determining that VSIG4 is involved in the kidney fibrosis in chronic kidney diseases.

The present disclosure provides a biomarker composition for diagnosing kidney diseases, including VSIG4 or a gene encoding the same as an active ingredient.

As used herein, the term "VSIG4 (V-set and immunoglobulin domain containing 4; VSIG4 gene ID: 11326)" refers to a B7 family-related protein, which is mainly expressed in macrophages and binds to CR1/CR3 of T cells for inhibition. It has been reported that VSIG4 is expressed not only in macrophages but also in liver, lung, heart, and abdominal cavity. VSIG4 is also known to be involved in various inflammatory responses, but its function other than suppression of functions of T cells is still unclear.

When various kidney damage or kidney fibrosis progresses, expression or activity of the VSIG4 protein or a gene encoding the same may increase, thereby enabling diagnosis of kidney diseases using the same.

The kidney diseases may be one or more diseases selected from the group consisting of diabetic nephropathy, hypertensive nephropathy, glomerulonephritis, polycystic kidney disease, urinary tract obstruction and other diseases. Kidney fibrosis is not limited thereto.

As used herein, the term "kidney fibrosis" refers to a finding in which kidney function is declining due to fibrosis of kidney tissues as a result of various causes such as excessive inflammatory responses, oxidative stress, and fibrosis of epithelial cells taking place in the kidney tissues. The kidney fibrosis itself is a lesion that shows various findings such as damage of renal tubular cells, epithelial mesenchymal transition, an increase in inflammatory responses, an influx of macrophages, proliferation of interstitial fibrosis cells, and deterioration in renal function and is also known as an important indicator of various kidney diseases.

As used herein, the term "diagnosis" refers to identification of the presence or characteristics of a pathological condition. For the purpose of the present disclosure, the diagnosis is to determine whether the kidney diseases occurs, specifically, to detect the kidney diseases by checking whether expression or activity of VSIG4 or a gene encoding the same increases in a sample isolated from a subject suspected of having kidney diseases compared to a normal control.

As used herein, the term "biomarker" refers to a substance that enables detection of the normal or pathological state of a living organism and changes in the state as an indicator that may detect changes in the body and may include organic biomolecules such as polypeptides, nucleic acids, lipids, glycolipids, glycoproteins, sugars (monosaccharides, disaccharides, oligosaccharides, etc.), and a use thereof enables diagnosis of the kidney diseases as in the present disclosure.

The biomarker according to the present disclosure shows the same result even in repeated experiments, and since the change in the expression level thereof derives a significant result, it may be considered as a highly reliable marker, such that the predicted result may be reasonably trusted.

The present disclosure provides a composition for diagnosing kidney diseases, including an agent for measuring the expression level of VSIG4 as an active ingredient.

The agent may be a primer or probe specifically binding to the VSIG4 gene, or an antibody, peptide, peptide mimetics, aptamer, or compound specifically binding to the VSIG4 protein, but is not limited thereto.

As used herein, the term "primer" refers to a nucleic acid sequence having a short free 3' hydroxl group, specifically, a short nucleic acid sequence capable of base pairing with a complementary template and functioning as a starting point for replication of template strands. The primer may initiate DNA synthesis in the presence of a reagent for a polymerization reaction (i.e., DNA polymerase or reverse transcriptase) and four different nucleotide triphosphates at an appropriate buffer and temperature.

The primers may be sense and antisense nucleic acids having a sequence consisting of 7 to 50 nucleotides as primers specific for the gene and may be added with additional features as long as they do not change the basic properties of the primers functioning as the starting point of DNA synthesis. PCR conditions as well as the length of sense and antisense primers may be appropriately selected according to techniques known in the art.

As used herein, the term "probe" refers to a nucleic acid fragment such as RNA or DNA corresponding to several to several hundred bases in length with capability of specifically binding to mRNA, and is also labeled such that it is possible to detect the presence or absence of a specific mRNA and expression level. The probe may be formed in the form of an oligonucleotide probe, a single strand DNA probe, a double strand DNA probe, and an RNA probe.

Appropriate probes and hybridization conditions may be appropriately selected according to techniques known in the art.

As used herein, "antibody" as a term known in the art refers to a specific immunoglobulin directed against an antigenic site. The antibody herein refers to an antibody that specifically binds to a protein encoded by the gene and may be prepared according to a conventional method in the art. The form of the antibody includes a polyclonal antibody or a monoclonal antibody, and any immunoglobulin antibody may be included. The antibody refers to a complete form having two full-length light chains and two full-length heavy chains. In addition, the antibody may include a special antibody such as a humanized antibody.

As used herein, the term "peptide" has high binding strength to a target substance without undergoing denaturation even upon heat/chemical treatment. In addition, it may be used as a fusion protein by being bound to other proteins due to its small molecular size. Specifically, since it may be used by being bound to a polymeric protein chain, it may be used as a diagnostic kit and a drug delivery material.

As used herein, the term "aptamer" refers to a type of polynucleotides consisting of a special type of single strand nucleic acids (DNA, RNA, or modified nucleic acid) that have a stable tertiary structure by itself with capability of binding to a target molecule with high affinity and specificity. As described above, the aptamer may specifically bind to antigenic substances in the same way as an antibody, but has higher stability than protein as well as a simple structure and is formed of polynucleotides that are easy to synthesize, such that it may be used in replacement of the antibody.

As described above, the aptamer may specifically bind to antigenic substances in the same way as an antibody, but has higher stability than protein as well as a simple structure, and is formed of polynucleotides that are easy to synthesize, such that it may be used in replacement of the antibody. The kit may be used to diagnose whether kidney diseases occurs by measuring the expression or activity level of VSIG4 or a gene encoding the same in a sample isolated from a subject suspected of having kidney diseases.

The kit for diagnosing kidney diseases may further include one type that is suitable for the analysis method or one or more other component compositions, solutions, or devices, and the kit may be a primer kit, a DNA chip kit or a protein chip kit, but is not limited thereto.

The kit may further include a substrate, a buffer solution, a secondary antibody labeled with a chromogenic enzyme or a fluorescent material, and a chromogenic substrate. The substrate may include a nitrocellulose membrane, a 96-well plate synthesized with a polyvinyl resin, a 96-well plate synthesized with a polystyrene resin, and a slide glass formed of glass. The chromogenic enzyme may include peroxidase and alkaline phosphatase, and fluorescein isothiocyanate (FITC) and rhodamine B isothiocyanate (RITC) may be used as the fluorescent material. In addition, as a chromogenic substrate solution, 2,2'-azino-bis(3-ethylbenzothiazoline-6-sulfonic acid) (ABTS), 0-phenylene diamine (OPD), or tetramethylbenzidine (TMB) may be used.

The present disclosure provides a method of providing information necessary for diagnosing kidney diseases, including measuring the expression or activity level of VSIG4 or a gene encoding the same in a sample isolated from a subject suspected of having kidney diseases; and comparing the expression or activity level of the VSIG4 or gene encoding the same with a normal control sample.

Through the information providing method, it is possible to determine as kidney diseases when the expression or activity level of VSIG4 or a gene encoding the same in the sample is higher than that of the normal control sample, and, by providing such the information, quicker and more effective treatment may be carried out by setting up a future treatment plan upon the onset of kidney diseases.

As used herein, the term "subject" refers to any animal, including human that has or may develop kidney diseases.

The sample isolated from the subject may include a sample such as tissues, cells, blood, serum, plasma, saliva, or urine that shows difference in the expression or activity level of VSIG4 or a gene encoding the same, preferably urine, but is not limited thereto.

The present disclosure provides a method of screening a therapeutic agent for kidney diseases, including treating a biological sample isolated from a subject with a test substance; measuring the expression or activity level of VSIG4 or a gene encoding the same in the sample treated with the test substance; and selecting a test substance in which the expression or activity level of the VSIG4 or gene encoding the same is reduced compared to a control not treated with the test substance.

The screening method is a method of comparing the increase or decrease in the expression or activity of the protein or a gene encoding the same in the presence and absence of a candidate therapeutic agent for kidney diseases and may be useful for screening a therapeutic agent for kidney diseases or a kidney fibrosis inhibitor, wherein a substance that reduces the expression or activity level of the VSIG4 or gene encoding the same may be selected as a therapeutic agent for kidney diseases or that for kidney fibrosis.

In the present disclosure, the protein expression or activity level may be measured by one or more methods selected from the group consisting of Western blot, enzyme linked immunosorbent assay (ELISA), radioimmunoassay (RIA), radioimmunodiffusion, Ouchterlony immunodiffusion, rocket immunoelectrophoresis, immunohistochemistry staining, immunoprecipitation assay, complement fixation assay, fluorescence activated cell sorter (FACS), and protein chip, but is not limited thereto.

In the present disclosure, the expression level of the gene may be measured by any one or more methods selected from the group consisting of polymerase chain reaction (PCR), reverse transcription PCR (RT-PCR), competitive RT-PCR, real-time RT-PCR, RNase protection assay (RPA), Northern blotting, and a DNA microarray chip, but is not limited thereto.

The present disclosure provides a pharmaceutical composition for preventing or treating kidney diseases, including an expression or activity inhibitor of VSIG4 or a gene encoding the same as an active ingredient.

The composition may prevent or treat the onset of kidney diseases by inhibiting the expression or activity of VSIG4 or a gene encoding the same.

The inhibitor may be selected from the group consisting of antisense nucleotides, small interfering RNA (siRNA), and short hairpin RNA (shRNA) complementarily binding to VSIG4 mRNA or may be selected from the group consisting of an antibody, peptide, peptide mimetics, aptamer, compound and natural products specifically binding to VSIG4, but is not limited thereto.

As used herein, the term "prevention" refers to any action that suppresses or delays the onset of kidney diseases, or at least one or more symptoms thereof, by administration of the pharmaceutical composition or health functional food composition according to the present disclosure. Also included is treatment of a subject in remission of the disease to prevent or avoid recurrence.

As used herein, the term "treatment" refers to any action that alleviates or beneficially changes kidney diseases, or at least one or more symptoms thereof, such as alleviation, reduction, or disappearance of the symptoms by administration of the pharmaceutical composition according to the present disclosure.

As used herein, the term "pharmaceutical composition" refers to a composition administered for a specific purpose and, for the purpose of the present disclosure, refers to administration to prevent or treat kidney diseases or at least one or more symptoms thereof.

The pharmaceutical composition according to the present disclosure may be prepared according to a conventional method in the pharmaceutical field. The pharmaceutical composition may be combined with an appropriate pharmaceutically acceptable carrier according to the formulation, and if necessary, it may be prepared by further including excipients, diluents, dispersants, emulsifiers, buffers, stabilizers, binders, disintegrants, or solvents. The appropriate carrier and the like do not inhibit the activity or properties of the inhibitor according to the present disclosure and may be selected differently depending on the dosage form and formulation.

As used herein, the term "pharmaceutically acceptable" refers to a state that is not toxic to cells or humans exposed to the composition.

The pharmaceutical composition according to the present disclosure may be applied in any dosage form and, more specifically, it may be used by being formulated into oral dosage formulations, external preparations, suppositories, and parenteral dosage formulations of sterile injection solutions according to conventional methods.

Of the oral dosage formulations, solid dosage formulation is in the form of tablets, pills, powders, granules, and capsules and may be prepared by mixing at least one or more excipients, for example, starch, calcium carbonate, sucrose, lactose, sorbitol, mannitol, cellulose, and gelatin while lubricants such as magnesium stearate and talc may be included in addition to simple excipients. In addition, the capsule formulation may further include a liquid carrier such as fatty oil in addition to the above-mentioned substances.

Of the oral dosage formulations, liquid formulation includes suspensions, solutions, emulsions, and syrups, and various excipients, for example, wetting agents, sweeteners, fragrances, and preservatives may be included in addition to water and liquid paraffin, which are commonly used simple diluents.

The parenteral formulation may include a sterile aqueous solution, non-aqueous solution, suspension, emulsion, freeze-dried formulation, and suppository. As non-aqueous solvents and suspending agents, propylene glycol, polyethylene glycol, vegetable oils such as olive oil, and injectable esters such as ethyl oleate may be used. As the base of the suppository, witepsol, macrogol, Tween 61, cacao butter, laurin fat, and glycerogelatin may be used. Not limited thereto, any suitable agent known in the art may be used.

In addition, the pharmaceutical composition according to the present disclosure may further be added with calcium or vitamins to enhance therapeutic efficacy.

In the pharmaceutical composition according to the present disclosure, the pharmaceutical composition may be administered in a pharmaceutically effective amount.

As used herein, the term "pharmaceutically effective amount" refers to an amount sufficient to treat diseases at a reasonable benefit/risk ratio applicable to medical treatment without causing side effects.

The effective dose level of the pharmaceutical composition may be differently determined depending on the purpose of use, the age, sex, weight and health status of a patient, the type of diseases, severity, drug activity, sensitivity to drug, administration method, administration duration, administration route and excretion rate, treatment period, elements including drugs blended or used in combination with, and other factors well known in the medical field. For example, although not constant, generally 0.001 to 100 mg/kg, preferably 0.01 to 10 mg/kg, may be administered once to several times a day. The above dosage does not limit the scope of the present disclosure in any way.

The pharmaceutical composition according to the present disclosure may be administered to any animal that the kidney diseases may occur, and the animal may include, for example, not only humans and primates, but also livestock such as cattle, pigs, horses, and dogs.

The pharmaceutical composition according to the present disclosure may be administered in an appropriate administration route depending on the type of the formulation and may be administered via various routes, either oral or parenteral as long as it is able to reach a target tissue. The administration method is not particularly limited and may be conducted in a conventional method such as oral, rectal or intravenous, muscle, skin application, respiratory inhalation, intrauterine dural or intracere-broventricular injection.

The pharmaceutical composition according to the present disclosure may be used alone for the prevention or treatment of kidney diseases or used in combination with surgery or other drug treatment.

In addition, the present disclosure provides a health functional food composition for preventing or ameliorating kidney diseases, including an expression or activity inhibitor of VSIG4 or a gene encoding the same as an active ingredient.

As used herein, the term "amelioration" refers to any action that alleviates or beneficially changes kidney diseases, or at least one or more symptoms thereof, such as alleviation, reduction, or disappearance of the symptoms by ingestion of the health functional food composition according to the present disclosure.

As used herein, the term "health functional food" includes food manufactured and processed using raw materials or components showing useful functionality for the human body in accordance with Act No. 6727 of the Functional Foods for Health Act, and for the purpose of the present disclosure, in addition to nutritional supply, it refers to foods with high medical and therapeutic effects that are processed to efficiently derive bioregulatory functions such as prevention of kidney diseases, body defense, immunity, and recovery.

Corresponding features may be substituted for the above-mentioned parts.

In the health functional food composition according to the present disclosure, the health functional food may be prepared in the form of powder, granules, tablets, capsules, syrups, or beverages for prevention or amelioration of kidney diseases. There is no limitation in the form that the health functional food may take, and the health functional food may be formulated in the same way as the pharmaceutical composition so as to be used as a functional food or added to various foods.

In the health functional food composition according to the present disclosure, the health functional food may include all foods in a conventional sense. For example, beverages and various drinks, fruits and processed foods thereof (canned fruit and jam), fish, meat and processed foods thereof (ham and bacon), breads and noodles, cookies and snacks, and dairy products (butter and cheese) are possible, and all functional foods in a conventional sense may be included. It may also include food used as feed for animals.

The health functional food composition according to the present disclosure may be prepared by further including a sitologically acceptable food additive and other suitable auxiliary ingredients commonly used in the art. The health functional food composition according to the present disclosure may be prepared by further including a sitologically acceptable food additive and other suitable auxiliary ingredients commonly used in the art. The items listed in the "Korean Food Additives Codex" may include, for example, chemical compounds such as ketones, glycine, calcium citrate, nicotinic acid, and cinnamic acid; natural additives such as persimmon pigments, licorice extracts, crystalline cellulose, kaoliang color, and guar gum; and mixed preparations such as sodium L-glutamate preparations, noodle-added alkali agents, preservative preparations, and tar color preparations.

The other auxiliary components may additionally include, for example, flavoring agents, natural carbohydrates, sweeteners, vitamins, electrolytes, coloring agents, pectic acid, alginic acid, organic acids, protective colloidal thickeners, pH adjusting agents, stabilizers, preservatives, glycerin, alcohols, and carbonating agents. In particular, monosaccharides such as glucose and fructose, disaccharides such as maltose and sucrose, polysaccharides such as dextrin and cyclodextrin, and sugar alcohols such as xylitol, sorbitol, and erythritol may be used as the natural carbohydrate, and natural sweeteners such as thaumatin and stevia extracts or synthetic sweeteners such as saccharin and aspartame may be used as the sweetener.

The effective dose of the inhibitor included in the health functional food according to the present disclosure may be appropriately adjusted according to the purpose of its use, such as prevention or amelioration of kidney diseases.

The health functional food composition has the advantages that there are no side effects that may occur during long-term administration of general drugs by using food as a raw material, and may be taken as an adjuvant for the prevention or amelioration of kidney diseases owing to excellent portability.

MODES FOR CARRYING OUT THE INVENTION

Hereinafter, to help the understanding of the present disclosure, example embodiments will be described in detail. However, the following example embodiments are merely illustrative of the content of the present disclosure, and the scope of the present disclosure is not limited to the following example embodiments. The example embodiments of the present disclosure are provided to more completely explain the present disclosure to those of ordinary skill in the art.

<Experiment Method>
1. Cell Experiment
1-1. Cell Culture
1-1-1. HK2 Cell Culture
HK2 cells (A TCC, Manassan, VA), immortalized human renal proximal tubule cells, were cultured by adding, in a DMEM medium (Mediatech Inc., Corning Subsidiary, Manassas, VA), 10% heat inactivated fetal bovine serum (Tissue Culture Biologicals, Tulare, CA, USA), 100 IU/mL of penicillin, and 100 mg/mL of streptomycin in a humid atmosphere in the presence of 5% $CO_2$ at 37° C.

HK2 cells were treated with low glucose (LG, 5.5 mM) and high glucose (HG, 55 mM), and expression of VSIG4 mRNA and protein was evaluated at 72 hours (VSIG4 gene ID: 11326). The purchased scrambled siRNA (control siRNA) and VSIG4 siRNA (z391g, Santa Cruz Biotechnology, Santa Cruz, CA) were each transfected by 200 MOI to suppress VSIG4 expression in HK2 cells.

To inhibit TGF-β expression, TGF-β-siRNA (Santa Cruz Biotechnology, Santa Cruz, CA, USA) was used, and 10 ng/mL of recombinant TGF-β (R&D systems, Minneapolis, MN, USA) was used for TGF-β stimulation experiment.

1-1-2. Podocyte Culture
The mouse podocyte cell line was mixed with 10% heat inactivated fetal bovine serum, 100 IU/mL of penicillin, and 100 mg/mL of streptomycin in RPMI culture medium and cultured in a humid atmosphere in the presence of 5% $CO_2$ at 37° C.

To evaluate VSIG4 expression, low glucose (LG, 5.5 mM) and high glucose (HG, 55 mM), 100 nM angiotensin II, 1.0 μg/mL and 3.0 μg/mL of Adriamycin were treated.

1-2. Evaluation on mRNA Expression
The medium in a plate in which cells are being cultured was removed and RNA was extracted using Trizol (Life Technologies, Gaithersburg, MD, USA). Reverse transcription (RT) was performed using a cDNA synthesis kit (Applied biosystems, Roche Inc., Foster City, CA, USA), mRNA expression was evaluated using polymerase chain reaction (PCR), and the expression level was corrected with β-actin or GAPDH. Each primer is as shown in Tables 1 and 2 below.

TABLE 1

| Human | Forward | Reverse |
|---|---|---|
| VSIG4 | AACTCCTGTCTCCAAGCCC (SEQ ID NO: 1) | GCAGTGCAGAAATAGGAGCC (SEQ ID NO: 2) |
| β-actin | GCCGGGACCTGACTGACTAC (SEQ ID NO: 3) | TCTTCTCCAGGGAGGAGCTG (SEQ ID NO: 4) |

TABLE 2

| Mouse | Forward | Reverse |
|---|---|---|
| VSIG4 | TCCCTGGCTTCCTTTCTTCT (SEQ ID NO: 5) | CCAAACCCAGGATTTCTCAA (SEQ ID NO: 6) |
| β-actin | GGACTCCTATGTGGGTGACG (SEQ ID NO: 7) | CTTCTCCATGTCGTCCCAGT (SEQ ID NO: 8) |

1-3. Western Blotting
Proteins obtained by treating cell lysates with RIPA buffer were quantified, and 20 μg of protein was separated using 8-15% SDS-PAGE. After separation of the protein by electrophoresis using 10% SDS-PAGE, the protein was transferred to a PVDF membrane (Millipore corporation bedford, USA) using a PAGE transfer buffer (Amersham Life Science, Arlington Heights, IL) at 270 mA for 4 hours, reacted overnight at 4° C. using a blocking solution (5% skim milk), and washed with Tris buffered saline with Tween-20 (TBS-T buffer; 10 mM Tris-Cl, pH 7.8, 150 nM Nacl, 0.05% Tween-20).

HK2 cells were treated with primary antibodies including anti-VSIG4, anti-Vimentin (1:500 dilution, Abcam, Cambridge, MA, USA) and anti-GAPDH (Aviva Systems Biology, San Diego, CA, USA), whereas podocytes were treated with primary antibodies including anti-VSIG4 (1:500 dilution, Abcam, Cambridge, MA, USA) and anti-beta actin (1:2000 dilution, Sigma, Saint Louis, MO, USA), diluted 1:200 to 1:1000 in TBS-T buffer and reacted at room temperature for 1 hour. After washing 3 times with TBS-T buffer, the secondary antibody was diluted 1:1000 and reacted at room temperature for 1 hour, and then the membrane was photosensitized using an ECL kit (Amersham Life Science), followed by photographing using Las-3000.

2. Animal Testing 2-1. Diabetic Model

Six-week-old male diabetic db/db mice (C57BLKS/J-leprdb/leprdb, Jackson Laboratory, Bar Harbor, ME) were purchased and kept under constant temperature ($23\pm2°$ C.) and humidity ($55\pm5\%$). Nondiabetic mice (db/m) as a control and diabetic mice (db/db) were each grouped into 6 and maintained for 12 weeks based on 8 weeks of age. After sacrificing mice at 12 weeks, the left kidney was excised for morphological analysis and then fixed in 4% paraformaldehyde solution, and only the cortex of the right kidney was excised and mixed with RNase inhibitor to be stored at $-70°$ C.

2-2. Unilateral Ureteral Obstruction Model

Experiments were carried out using 8-week-old C57/BL6 mice, divided into a control and a unilateral ureteral obstruction (UUO) group. To prepare a UUO model, after laparotomy, two portions of the left ureter was tied up with 6-0 silk thread, the ureter was cut off, and the mice were sacrificed to remove the kidney after maintaining for 14 days, wherein tissues were divided and fixed in 4% paraformaldehyde solution for morphological analysis, and the remaining portions were mixed with RNase inhibitor after peeling only the cortical region so as to be stored at $-70°$ C.

10 [133]2-3. Adriamycin-Induced Renal Injury Model

Nine Balb/c male mice (RaonBio, Yongin Korea) that are 6 weeks old were assigned to the control and the Adriamycin-administered group, respectively. The 11 mg/kg of Adriamycin was administered once into the tail vein and maintained under the same condition as described above for 4 weeks. At 4 week, mice were sacrificed, wherein the urine and kidney extraction procedures were performed in the same manner as described above.

2-4. Senescent Model

Experiment was carried out by purchasing 6-week-old male diabetic db/m and db/db mice (C57BLKS/J-leprdb/leprdb, Jackson Laboratory, Bar Harbor, ME), each consisting of 36. With a total of 5 times from 8 weeks of age to 24 weeks of age with 4 weeks apart, 6 mice each were sacrificed at the last 38 weeks of age, and urine was collected for 6 hours before sacrifice. Animal maintenance conditions and urine culture methods are the same as described above.

25 [139]2-5. Urine

Urine was collected and stored in a metabolic cage for 24 hours before sacrificing the mice. VSIG4 (Bioassay Technology Laboratory, Shanghai, China) in the stored urine was measured using ELSIA, followed by correction with creatinine.

2-6. Evaluation on mRNA Expression

After homogenizing the cortical region of the kidney, RNA was extracted using a TRI reagent (GibCo BRL, USA). cDNA synthesis was conducted by reverse transcription using a kit (Applied Biosystems, Roche, USA). Quantitative RT-PCR was performed by denaturation using SYBR Green technology in a LightCycler 1.5 system (Roche diagnostics Corporation, Indianapolis, IN) by 22-30 cycles at 95° C. for 10 seconds, followed by annealing at 53° C. (VSIG4) and 57° C. ($\beta$-actin) for 4 seconds.

Primers of VSIG4 and $\beta$-actin are shown in Table 2 above.

2-7. Evaluation of Progression of Nephropathy Through Pathological Biopsy and Immunocytochemistry The tissue fixed with paraformaldehyde was sectioned to a thickness of 4 $\mu$m, paraffin was removed with xylene, and then hydration was sequentially followed in 100, 95, and 70% alcohol. The antigen was exposed by boiling with a citrate buffer (pH 6.0) at 80° C. for 30 minutes, and then treated with 3% MeOH—$H_2O_2$ for 10 minutes to remove endogenous peroxidase.

In order to prevent non-specific protein binding, it was left in horse serum at room temperature for 20 minutes. Anti-VSIG4 (R&D system, Minneapolis, MS) was diluted 1:100, reacted overnight at 4° C., washed three times with tris buffer, underwent a secondary antibody reaction using a secondary antibody kit (anti-goat HRP-DAB cell & tissue staining kit) and staining with diaminobenzidine, and then encapsulated after counterstaining with hematoxylin to complete slides.

3. Prediction of Kidney Damage in Patients with Diabetic Kidney Disease

A total of 131 patients were included, with type 2 diabetes. Measured was concentration of serum creatinine ($1.95\pm1.61$ mg/dL), albuminuria ($1.60\pm2.33$ g/gCr) in urine, and urinary VSIG4 ($6.35\pm8.85$ ng/mgCr), which were indicators of kidney function at the time of registration. The glomerular filtration rate was calculated using the CKD-EPI formula based on serum creatinine. Thereafter, 3 years of measurement for serum creatinine of the patients was followed to evaluate the degree of deterioration in the kidney function. Selected as the primary indicator was a 30% decrease in the glomerular filtration rate or a case receiving renal replacement therapy such as dialysis or transplant as an indicator for kidney functions after 3 years.

4. Statistical Processing

The statistical program SPSS 25.0 was used for all experimental results, which were defined as being statistically significant when P<0.05.

<Experiment Result>

1. Identification of VSIG4 Expression Patterns in Kidney Cells Stimulated with High Glucose 1-1. Identification of VSIG4 Expression Patterns in Renal Tubular Cells Stimulated with High Glucose 1) When HK2 cells, which are proximal cells among human renal tubular cells, were treated with low glucose (LG, 5.5 mM) and high glucose (HG, 55 mM), it was found that expression of VSIG4 mRNA and protein increased under the high glucose (HG) at 72 hours (FIG. 1).

2) When treated with high glucose (HG), VSIG4 and vimentin increased, and when VSIG was inhibited using siVSIG4, the synthesis of vimentin decreased (FIG. 2). Here, it may be found that VSIG4 is involved in the fibrosis that takes place under condition with high glucose (HG).

3) It was found that VSIG4 expression decreased when renal tubular cells were treated with siTGF-$\beta$ after high glucose treatment, and VSIG4 expression increased when TGF-$\beta$ was treated (FIG. 3).

1-2. Identification of VSIG4 Expression Patterns in Podocytes Stimulated with High Glucose When podocytes, which play an important role in the development and progression of diabetic nephropathy, were stimulated with high glucose and angiotensin II, the main substances of kidney damage, the expression of VSIG4 mRNA and protein increased compared to that under low glucose (FIG. 4).

2. Identification of VSIG4 Expression Patterns in db/db Mice

In db/db mice, a type 2 diabetic model, intrarenal VSIG4 mRNA expression significantly increased compared to nondiabetic db/m mice, and a significant difference was also observed in the immunochemical staining of VSIG4 protein (FIG. 5). Thereby, it may be determined that VSIG4 is involved in the progression of diabetic nephropathy.

In db/db mice, a type 2 diabetic model, VSIG4 protein expression in urine significantly increased compared to nondiabetic db/m mice, and at this time, there was a significant correlation with albumin (FIG. 6). Therefore, it may be found that VSIG4 is involved in the progression of type 2 diabetic nephropathy.

3. Identification of VSIG4 Expression Patterns in a UUO Model

As a result of evaluating VSIG4 mRNA expression in the UUO model, which is a model of kidney fibrosis, it was found that the expression of VSIG4 mRNA in the kidney increased in the UUO model compared to the control, with a stark difference also in the immunochemical staining. In addition, VSIG4 protein expression in urine was significantly elevated in the UUO model compared to the control (FIG. 7).

Thereby, it may be expected that VSIG4 is involved in the progression of kidney fibrosis.

4. Identification of VSIG4 Expression Patterns in an Adriamycin-Induced Renal Injury Model.

1) When Adriamycin was injected for 4 weeks, albuminuria and VSIG4 protein expression significantly increased for 24 hours. In addition, VSIG4 mRNA expression in kidney tissues significantly increased as well (FIG. 8).

2) When 1.0 µg/mL and 3.0 µg/mL of Adriamycin were administered to podocytes for 12 hours and 24 hours, respectively, expression of VSIG4 mRNA and protein increased over time at both concentrations (FIG. 9).

Based on the above results, it was found that VSIG4 is related in the Adriamycin-induced renal injury model.

5. Identification of VSIG4 Expression Patterns in the Senescent Model

1) In db/m mice, which are normal mice, the amount of VSIG4 in urine did not show significant changes until 24 weeks, but increased more than 3 times in the 38-week-old mice. At this time, albuminuria, which is a representative indicator of kidney damage, also showed a similar pattern (FIG. 10).

2) In db/db mice, a type 2 diabetic mouse model, the amount of VSIG4 and albuminuria in the urine increased from the beginning, and the expression level increased over time.

Based on the above results, it was found that the VSIG4 pattern is related to senescence in normal mice and type 2 diabetic mice.

6. Identification of VSIG4 Expression Patterns in a Patient with Type 2 Diabetic Nephropathy In 131 patients with type 2 diabetes and nondiabetes, VSIG4 in urine had a significant positive correlation with albuminuria. For the indicator for the kidney function after 3 years, including the 30% decrease in the glomerular filtration rate or a probability of receiving renal replacement therapy (dialysis or transplant), it was determined that the ROC AUC value was a meaningful indicator to a degree similar to albuminuria (FIG. 11).

As described above, a specific part of the content of the present disclosure is described in detail, for those of ordinary skill in the art, it is clear that the specific description is only a preferred embodiment, and the scope of the present disclosure is not limited thereby. In other words, the substantial scope of the present disclosure is defined by the appended claims and their equivalents.

The invention claimed is:

1. A method of screening a therapeutic agent for treating a kidney disease, comprising:

isolating a biological sample from a patient suspected of having the kidney disease;

treating the biological sample with a test substance;

measuring an expression level of VSIG4 mRNA in the biological sample treated with the test substance by reverse transcription polymerase chain reaction (RT-PCR) using a forward primer having the nucleotide sequence set forth in SEQ ID NO: 1 and a reverse primer having the nucleotide sequence set forth in SEQ ID NO: 2;

measuring an expression level of the VSIG4 protein in the biological sample treated with the test substance by enzyme-linked immunosorbent assay (ELISA) using an anti-VSIG4 antibody; and selecting the test substance as a therapeutic agent for treating the kidney disease when the expression level of VSIG4 or a gene encoding VSIG4 is reduced in the biological sample treated with the test substance as compared to a control sample not treated with the test substance, wherein the kidney disease is selected from the group consisting of diabetic nephropathy, hypertensive neph- ropathy, glomerulonephritis, polycystic kidney disease, and urinary trace obstruction.

* * * * *